United States Patent [19]

Cisney et al.

[11] 3,931,335
[45] Jan. 6, 1976

[54] PROCESS FOR SELECTIVELY PRODUCING 4,4-MONOTHIODIPHENOLIC COMPOUNDS IN HIGH YIELDS

[75] Inventors: Merle E. Cisney, Camas; Robert A. Damon, Vancouver, both of Wash.

[73] Assignee: Crown Zellerbach Corporation, San Francisco, Calif.

[22] Filed: Aug. 26, 1974

[21] Appl. No.: 500,806

[52] U.S. Cl. ............................................. 260/609 F
[51] Int. Cl.² ....................................... C07C 149/36
[58] Field of Search ............................... 260/609 F

[56] References Cited
UNITED STATES PATENTS

| | | | |
|---|---|---|---|
| 2,760,988 | 8/1956 | Schetty et al | 260/609 F |
| 2,760,989 | 8/1956 | Moore | 260/609 F |
| 3,057,926 | 10/1962 | Coffield | 260/609 F |
| 3,390,190 | 6/1968 | Curtis et al | 260/609 F |
| 3,553,269 | 1/1971 | Richmond | 260/609 F |
| 3,718,699 | 2/1973 | Fujisawa et al | 260/609 F |
| 3,726,928 | 4/1973 | Fuchsman | 260/609 F |

OTHER PUBLICATIONS

J. W. Mullin, "Crystallization" pp. 159–162 (1961).

*Primary Examiner*—Lewis Gotts
*Assistant Examiner*—D. R. Phillips

[57] ABSTRACT

A process is provided for the formation of 4,4'-monothiodiphenolic compounds, in high yields, and in a selective manner, through the use of a novel reaction system. More specifically, a nonsterically hindered phenol and sulfur dichloride are reacted in the presence of initiation promoter and solvent portions, respectively, to produce the above 4,4'-monothiodiphenolic product.

27 Claims, No Drawings

PROCESS FOR SELECTIVELY PRODUCING 4,4-MONOTHIODIPHENOLIC COMPOUNDS IN HIGH YIELDS

BACKGROUND OF THE INVENTION

Reactions of phenolic compounds and sulfur halides, in general, to form a broad spectrum of the reaction products too numerous to mention, are well-known in the prior art. Many of these prior art reactions provide for the formation of a mixture of reaction products. However, others require the reaction of specific phenols and sulfur halides while maintaining a myriad of reaction conditions, to form specific thiophenolic materials. More specifically, the product recovered on contacting a phenol and sulfur dichloride generally contains a combination of mono- and poly- sulfides, chlorinated phenols, sulfonium compounds, polymeric materials, and the like. However, if a specific 4,4'-monothiodiphenolic compound, such as 4,4'-thiodiphenol, were the desired product, any other materials present would be considered by-products and would require separation from the total material produced and recovered. Recovery is a particularly acute problem in the case of the polysulfide by-products since they are formed as part of the solid, crystalline product phase along with the desired 4,4'-monothiodiphenolic product. Thus, when polysulfides are present, further recovery steps are necessary to separate the respective solid phases. Unlike their monothiophenolic counterparts, polysulfides contain relatively weak sulfur-to-sulfur bonds. Therefore, on polymerization of these polysulfides, the resultant polymeric product will be relatively weak because of this defective bonding characteristic.

The yield of specific monothiodiphenols formed by the direct contact of a phenolic compound and a sulfur halide, according to the prior art processes, in cases where the formation of specific materials is desired, is relatively poor. And, in addition to the aforementioned drawbacks, known processes teach that relatively long contact times are generally required for specific product formation, in relatively poor yields. Furthermore, due to the relatively long contact times exhibited by the prior art processes, difficulties will result in conducting a continuous reaction, in an efficient manner, to selectively form high yields of specific 4,4'-monothiodiphenols. Moreover, the economic feasibility of such a process is highly questionable.

Many of the aforementioned phenolic reactions have been employed in preparing either stabilizers or antioxidants. For example, U.S. Pat. No. 1,849,489 to Howland describes the formation of a class of chemical compounds "adapted to retard deterioration of rubber." These compounds include sulfides of phenol. An example of this reaction is shown on page 2, beginning on line 55, wherein a relatively high concentration of phenols is reacted with a sulfur chloride compound in a chloroform solvent. A low yield of phenol sulfides was seemingly formed after a 2-hour reaction period. Furthermore, any combination of sulfides, polysulfides or isomers thereof provides an acceptable reaction product for use therein. A high specific product yield is not required in the above formation process.

Another process which describes the production of sulfur-containing phenols useful as antioxidants is found in U.S. Pat. No. 3,678,115 to Fujisawa et al. In this case, the production of a sulfur-containing sterically-hindered phenol, i.e., 4,4'-thiobis(2,6-di-t-butyl phenol) is disclosed. The formation of the above sterically-hindered phenolic product is conducted according to an entirely different reaction system than is provided for its nonhindered counterpart. The Fujisawa process, for instance, includes reacting a high concentration (greater than 25% by weight) of 2,6-di-t-butyl phenol (a hindered phenolic reactant) employing either sulfur chloride or sulfur dichloride, and requiring, in the sulfur dichloride reaction, a reaction period of greater than about 24 hours. The use of relatively high concentrations of phenol causes additional problems in mass transport of the product mixture formed, thereby further increasing the total reaction time and, in case of reaction of a phenol and sulfur dichloride, promotes the formation of a noncrystalline phase in the reaction system which is detrimental to the facilitation of high yields of the desired product. Example 1 of Fujisawa indicates that the 4,4'-thiobis(2,6-di-t-butyl phenol) was present in only a 23% yield after an initial 18-hour reaction period, 53% of the total product formed being polysulfides. Thereafter, in order to provide a higher yield of the monothiophenolic product, the polythiobisphenols present in the mixture were further reacted for about 14 hours with a strong base in order to cleave the sulfur bridges to form of mercapto compound which, in turn, recombines with the unreacted phenolic reactant to form additional amounts of the desired 4,4'-thiobis product.

U.S. Pat. No. 2,139,766 to Mikeska et al. provides for the formation of a dialkyl diphenol thio ether compound by the relatively limited reaction of a high concentration of phenol with sulfur dichloride in a carbon disulfide solvent. The product, which is then added to a mineral lubricating oil, acts as an antioxidant. As previously discussed with respect to the above cited patents, when the end use of a thiodiphenolic product is as an antioxidant, selectivity in forming a high yield monothiodiphenolic product, having a minimum amount of by-products, is not required.

In another prior art method (see U.S. Pat. No. 3,296,310 to Gilbert), the process for producing thiobis phenols is conducted by reacting elemental sulfur with the phenol in the presence of a halogen. The process is claimed by the inventor as an improvement over methods which employ the reaction of phenol with sulfur halide, such as sulfur chloride or sulfur dichloride. In this latter case, the halogen employed as a catalyst is either iodine or bromine, not chlorine. Selectivity, yield and reactor time problems previously expressed are again present in the Gilbert process. In fact, many of the aforementioned problems are further magnified since a mixture of thiobis phenols are formed in which the sulfur atoms are attached to the phenol in either the ortho- or para- positions, as opposed to selectively providing a predominant attachment in only the para- position.

U.S. Pat. No. 2,425,824 to Peters et al. provides a process in which sulfur halides are reacted with a high concentration of a phenolic compound, in a mole ratio of from about 1.25 to 1.75:2.0, and preferably 1.5:2.0. Poor selectivity and yield are evident on examining the product material. The products formed are continuously discharged from the reactor. The use of sulfur monochloride, sulfur dichloride, or mixtures thereof, respectively, as the reactant herein, is shown to be equivalent. As described in column 3, beginning at line 2, "the important point of the process is to at all points maintain the desired narrow limits of ratios of the reactants . . . " Therefore, one would conclude that only by employing the above specified reactant ratio could a continuous phenolic-sulfur chloride reaction process be maintained.

U.S. Pat. No. 3,057,926 to Coffield relates to the production of an antioxidant wherein a substituted phenol is reacted with either sulfur monochloride or sulfur dichloride to produce a substituted thio bis phenol compound having one or more sulfur atoms attached to the respective rings. Stoichiometric amounts, 2:1 mole ratios of phenol per mole of sulfur halide, and high concentrations of phenol are employed in the Coffield process. The previously enumerated problems associated with selectivity, yield, reaction time, and high concentration are once more present herein. In addition, the patent does not distinguish between the use of the respective sulfur halides as reactants. Finally, complicated and arduous addition techniques are provided in the examples of Coffield in order to produce, as in Example 2, a thio bis phenolic product.

Finally, U.S. Pat. No. 3,390,190 to Curtis et al. provides a process for purifying a conventionally produced thiophenolic product prepared by the reaction of phenol and sulfur dichloride in toluene. The final product is obtained by refluxing the initial crude reaction mixture, separating a tar phase, and purifying the crude product so obtained by dissolving it in an alkaline solution of a weak, inorganic base, such as sodium carbonate. Curtis provides a 4,4'-dihydroxy diphenyl sulfide material produced, as illustrated in Example 1, in a 55.2% yield based on theory. Furthermore, after purification thereof, the actual yield based on starting materials of the final purified product is about 47%, due to losses in product incurred during the above purification. And, even after performing these elaborate purification steps, which require a substantial period of time to complete, the amount of polysulfides present in the final 4,4'-isomeric product recovered (see Tables III--IV) is still 2.4 -3.5% by weight.

SUMMARY OF THE INVENTION

In contradistinction to prior art processes, the subject process, which includes the reaction of a phenolic compound and sulfur dichloride, provides for the selective formation of high yields of the 4,4'-monoisomer of various thiodiphenolic compounds, while producing only a minimum amount of undesirable by-products, i.e., polysulfides, non-para-sulfur-substituted thiodiphenols, chlorinated phenols, sulfonium compounds, and polymeric materials. Since the removal of polysulfides from the recovered product is particularly troublesome, the formation of a minimum amount thereof is desirable. Preferably, the amount of polysulfides present in the product recovered is less than 1%, and more preferably less than 0.5% by weight, based on the total weight of product material recovered. The selectively-produced 4,4'-monothiodiphenol is recovered, on substantial completion of the phenolic compound-sulfur dichloride reaction step, without requiring any additional reaction steps, in hereinafter defined yields of at least about 70% by weight, and preferably at least about 80% by weight. In determining the product conversion, the amount of phenolic compound actually consumed or used is derived by subtracting the amount of recovered, unreacted phenolic compound (since an excess of phenol is employed) from the total amount of phenol charged to the system. The selectivity, i.e., the weight percentage of 4,4'-mono-isomer present in the reaction product, is at least about 80% by weight, based on the total weight of recovered material, and preferably at least about 90% by weight.

The process of the present invention is characterized by a novel reaction system. The presence of this reaction system at the outset of the reaction is necessary for selective formation of high yields of the above described 4,4'-monothiodiphenolic product. More specifically, this novel reaction system is comprised of a reactant portion including the hereafter described phenolic compound and sulfur dichloride, an initiation promoter portion including crystals of the desired 4,4'-monothiodiphenolic product and a catalytic amount of anhydrous hydrogen chloride and, finally, a solvent portion, as later defined.

The subject selective reaction process provides for the reaction of a sterically nonhindered phenolic compound and sulfur dichloride in the presence of the above initiation promoter and solvent portions, respectively. In addition, by preferably providing a relatively low concentration of the subject phenolic compound, it has been discovered that the yield and selectivity of the reaction are unexpectedly increased while the amount of polysulfides in the recovered product is decreased. Under preferred conditions, such as when the product formed by the reaction system of the present invention is continuously produced and recovered, a substantial reduction in contact time, i.e., the time required to produce the thiodiphenolic material after the reaction system is formed, is provided. More specifically, contact times of not more than about 0.5 hour, and preferably not more than about 0.25 hour, are provided for formation of the requisite 4,4'-isomer.

DESCRIPTION OF THE PREFERRED EMBODIMENTS

The phenolic compounds, as defined for purposes of this invention, which are included in the reactant portion of the reaction system, may comprise any compound having a hydroxyl group substituted on a benzene ring, which will effectively direct the para- substitution, with respect to the pendant hydroxy group, of a single sulfur atom, to the selective formation of a 4,4'-monothiodiphenolic compound. For example, if phenol, the most preferred compound herein, were employed as the phenolic compound in the reaction system of the present invention, the predominant reaction would provide for a single sulfur atom to be selectively substituted on a phenol ring in the 4-position, a second phenol group then being attached at its 4-position to the pendant sulfur of the above formed phenol monosulfide intermediate, the resulting product being 4,4'-thiodiphenol (hereinafter TDP).

Various unsubstituted and mono- or di-substituted phenolic compounds can be employed in the reactant portion of this invention provided that the latter compounds are mono- or di-substituted in only the ortho- (2- or 2,6-) position, and, additionally, are not sterically hindered. Preferably, the mono- or di-ortho-substituted phenolic compounds employed in the present invention are characterized by the fact that the pendant groups substituted on the phenol ring include lower alkyl groups having from 1 to 3 carbon atoms, the total number of carbon atoms present in the alkyl groups of the substituted phenolic compound being from 1 to 5. More preferably, examples of the nonsterically hindered ortho- , mono-, and di-substituted phenolic compounds contemplated herein include phenol, o-cresol, 2,6-xylenol, and the like.

The second component of the subject reactant portion is sulfur dichloride. The dichloride, and not the monochloride, is sepcifically required for purposes of forming the subject compounds. It is preferred that the sulfur dichloride employed have a purity greater than about 98% by weight.

It is required in the high yield, selective process for preparing 4,4'-monothiodiphenolic compounds that the reaction of the above defined phenolic compounds and sulfur dichloride be conducted in the presence of an initiation promoter. The initiation promoter is comprised of two components. The first of these components is a crystalline additive of the particular 4,4'-monothiodiphenolic product to be formed. The second component is a catalytic amount of anhydrous hydrogen chloride. Both of these components must be present in the reaction system in order for the selective process of this invention to proceed. For example, in the case of the formation of the previously identified TDP compound, TDP crystals are provided. The actual amount of monothiodiphenol crystals present is dependent on the solvent, the reaction temperature, and the concentration and nature of phenol compound employed. Preferably, the product crystals are present in an amount sufficient for saturation of the reaction system, and more preferably, an amount in excess of that required for saturation.

It is also necessary that a catalytic amount of anhydrous hydrogen chloride be present in the initiation portion to provide efficient promotion of the selective reaction process. Preferably, the reaction system is saturated with the anhydrous hydrogen chloride in order to promote maximum selectivity and yield. The actual amount of hydrogen chloride needed for saturation is dependent on the solvent employed, the reaction temperature, the concentration of phenol, and the reaction pressure.

The subject reaction is conducted in the presence of a solvent portion which is substantially nonreactive with respect to the reactant, initiation promoter, and product phases, respectively, but is capable of at least partially dissolving the initiation and product portions, while substantially dissolving the reactant portion. A more accurate characterization of the suitability of a given reaction medium is the "solubility parameter" ($\delta_s$) of the solvent. A detailed description of solubility parameters can be found in an article entitled "Solubility Parameters for Film Formers", by H. Burrell, which appeared in the Official Digest, October 1955, on pages 726–758. Another article entitled "New Values of the Solubility Parameters from Vapor Pressure Data", by H. L. Hoy, in the Journal of Paint Technology, Volume 42, No. 541, February 1970, pages 76–118, updates the Burrell work. In general, a solvent is employed which is a saturated compound having a solubility parameter as shown in Table 7, page 742, of the Burrell article, and pages 91–102 of the Hoy article, of at least 7.0 $(Cal/cc)^{1/2}$ and up to about 9.0 $(Cal/cc)^{1/2}$, and preferably at least about 7.5 $(Cal/cc)^{1/2}$ and up to about 8.5 $(Cal/cc)^{1/2}$. In addition, the above preferred solvents exhibit, as explained in the above Burrell article, a low degree of hydrogen bonding. More preferably, compounds such as cycloaliphatics, aliphatics, halogenated aliphatics, substituted or unsubstituted, and mixtures thereof, are employed as solvents herein. More specifically, compounds such as cyclohexane, methylcyclopentane, methylcyclohexane, hexane, and heptane, are the solvents most preferred for use in the process of the invention herein.

The reaction system of the present invention can be formed by various techniques which provide for high dispersion, good dilution, and intimate mixing of the respective components. However, the preferred method of preparing the subject 4,4'-thiodiphenolic compound of this invention includes directly admixing the respective reactants, initiation promoter, and solvent portions together, one with the other, to produce the reaction system of this invention. Thereafter, the phenolic compound and sulfur dichloride can be reacted, continuously or batch-wise, in the presence of the above initiation promoter and solvent portions, to selectively produce high yields of thiodiphenolic compounds having a relatively small amount of by-products, especially polysulfides. In any case, once the reaction system is established, high yields of the 4,4'-isomer can be selectively and expeditiously produced.

Although the novel process of this invention may be conducted quite readily in a batch or semi-batch system, it is a preferred embodiment of this novel process that the reaction herein be selectively conducted by continuously adding the reactant portion to the reaction system while, at the same time, continuously drawing off the subject product formed. Thus, as previously indicated, the contact time of the subject reaction can be substantially reduced.

In order to specifically effectuate a preferred reaction environment, certain select conditions are established. For instance, it has been discovered that if a low concentration of phenol is provided in the reaction system, the reaction selectivity will favor crystalline formation, and not, as in the prior art processes, the formation of undesirable, noncrystalline by-products. Therefore, it is preferred that a concentration of phenolic compound in the reaction system be maintained at least at about 0.5 weight percent, based on the total weight of the reaction system, and up to about an amount of phenolic material which would result in the formation of a substantial amount of noncrystalline by-products, the actual concentration of phenolic reaction product being dependent on the solvent employed and the reaction temperature. More preferably, a concentration of at least about 1% by weight and up to about 20% by weight of the subject phenolic compound is employed herein.

It is a further preferable embodiment of this invention that the amount of phenol with respect to sulfur dichloride be maintained at a sufficiently high level. For example, the stoichiometric mole ratio of phenol to sulfur dichloride is 2:1. Unfortunately, when the above mole ratio of reactants is employed in the present system, the reaction selectivity will result in higher by-product formation. Preferably, therefore, the mole ratio of phenolic compounds to sulfur dichloride in the reactant portion of the reaction system is maintained in at least a minimum ratio of 3:1, and more advantageously, a mole ratio of at least 4:1, up to a ratio of about 10:1, can be employed herein.

The pressure in the reactor during the selective reaction of the present invention, based on economic considerations, is generally maintained at an atmospheric level. However, superatmospheric pressure may be employed up to about 500 psig. In this latter case, a faster reaction rate is generally provided.

The reaction temperature employed depends on the concentration and the nature of the phenolic compound as well as the reaction solvent employed. For optimum results, the reaction temperature is greater than the freezing point of the respective phenolic compound reaction solvent, and less than the temperature at which a substantial amount of undesirable, noncrystalline by-product will be produced. For example, if cyclohexane were the solvent in a phenol-sulfur dichloride reaction system, the preferred temperature range would be from about 20° C. to 30° C.

A sufficient degree of agitation should be provided so that the reactant and initiation promoter portions are thoroughly dispersed in the solvent portion. More specifically, mixing intensity must be maintained to insure that sufficient interfacial contact between the respective portions is maintained.

The following are illustrative examples showing the typical results obtained by the process of the present invention:

EXAMPLE 1

This example illustrates the continuous process of the subject invention.

A reaction vessel for continuously producing 4,4'-thiodiphenolic compounds was constructed from a 12-inch long section of 6-inch (i.d.) glass pipe mounted vertically and closed at its respective ends by a pair of flat plates. The vessel was equipped with baffles, a thermocouple, cooling coils, and a stirrer with a 3-inch pitched blade stirrer. The upper plate was fitted with two inlet tubes for introducing the respective reactant solutions, and an outlet tube for removing excess gaseous hydrogen chloride. The bottom plate was fitted with an overflow tube for removal of the reaction product formed. The overflow tube was designed to permit variation in the depth of the reaction system. Solutions of the phenolic compound and sulfur dichloride reactants were individually prepared before use and stored separately. The solutions were then delivered to the reaction vessel at suitable rates employing adjustable metering pumps. The combination of concentration of reagents and individual pumping rates permitted various ratios of reactants to be selected, and the pumping rates in conjunction with the height of the overflow outlet tube in the reactor permitted variation of the contact times of the respective reactants. A continuous run was made in which a solution of phenol in cyclohexane was prepared by dissolving 454 g of phenol (4.83 moles) in sufficient cyclohexane to form a total of 1 gallon of the above solution by volume. The phenol solution was then saturated with anhydrous hydrogen chloride gas. The reactant solution contained 14.7% by weight phenol and 0.22% by weight hydrogen chloride. A second reactant solution was prepared by dissolving 124.5 g of sulfur dichloride in sufficient cyclohexane to make a solution totaling about 1 gallon by volume. This solution contained 4.15% sulfur dichloride by weight. The two reactant solutions were stored in separate containers. The containers were connected through separate, adjustable, metering pumps to the inlet tubes in the reactor top.

The reaction was commenced by running cool water through the cooling coils, starting the stirrer, injecting a slow stream of nitrogen into and through the reactor, placing in the reactor about one liter of the above phenol-cyclohexane solution, and then adding to the solution 4,4'-thiodiphenol crystals in an amount in excess of that which is required for saturation.

The metering pumps were started and each was adjusted to deliver 50 ml per minute of the respective phenol and sulfur dichloride solutions. Under these conditions of concentration and pumping rate, the phenol was delivered at twice the stoichiometric requirement of the sulfur dichloride (at about a molar ratio of 4:1). The stirrer was maintained at about 1200 to 1400 revolutions per minute and the water flow was regulated to control the reaction slurry temperature at about 25° C. to 28° C. With the overflow outlet tube adjusted to three inches above the reactor vessel bottom plate, the retained volume of the slurry in the reactor during agitation was 700 to 800 ml. At a total pumping rate of about 100 ml per minute, this provided a contact time of about 0.01 to 0.13 hour.

Once about one gallon of 4,4'-thiodiphenol product had passed through the reactor, the reaction system was essentially at "steady state". The TDP product slurry was collected and filtered, and the accrued product was extracted with fresh, hot cyclohexane. The dried product was a colorless microcrystalline solid, which weighed about 118 g and represented about 91% of the expected theoretical conversion to 4,4'-thiodiphenol. Moreover, the 4,4'-monothiodiphenol selectivity was derived by determining the percent by weight of 4,4'-isomer in the total crude product. More specifically, gas-liquid chromatographic analysis (GLC) of subject product was performed using a Hewlett-Packard Model No. 5750 chromatograph equipped with a thermal conductivity detector. The conditions employed in the above analysis were as follows:

1. Column — 10 feet, 10% SE 30 on high performance Chromosorb W (AW-DMSC)
2. Carrier Gas — helium at 30 cc per minute
3. Detector — thermo conductivity — 175 milliamps
4. Inlet and Detector Temperature — 270° C.
5. Sample Size — 10 microliters of ether solution thereof containing about 16 g of product per liter
6. Procedure — sample was injected into a preheated column (100° C.), the temperature being retained at that level for six minutes. The temperature in the column was then raised, at the rate of 20° C. per minute, to 250° C. and maintained at that temperature for a period of about 11 minutes. The chromatographic data was then read and interpretted.

The selectivity of the above TDP material was 97%.

The conversion to 4,4'-monothiodiphenol product, based on the amount of consumed phenolic compound, was calculated as follows:

$$\text{Conversion} = \frac{\text{Moles of phenol actually converted to product}}{\text{Moles of phenol consumed by the process of the present invention}} \times 100$$

The actual yield of 4,4'-monothiodiphenolic material produced by the subject formation process is calculated by multiplying "conversion" times "selectivity". For example, in the above case the yield was about 88.3%.

As previously described, polysulfides present in the solid final product are difficult to remove. Therefore, the smaller the amount of polysulfide present, the better the quality of the final product recovered. Polarographic analysis is used to determine the polysulfide contents of the material formed by the subject process.

A Heath polarograph MOdel EUA 19-2 and XY Recorder HP Model 2V-2 were employed to conduct the above polarographic study. The average polysulfide content of the material produced during the course of the above run was about 0.4%.

The above results clearly demonstrate a direct, continuous process for selectively producing the subject 4,4'-monothiophenols in high yields, with a minimum amount of by-products, the requisite reaction system being employed to facilitate the process of the present invention. In addition, contact time is significantly reduced.

EXAMPLE 2

The example illustrates the batch process of the subject invention.

A solution of 79 g of phenol (0.84 mole) in 800 cc of cyclohexane was added to a 3-liter flask. The solution was saturated with anhydrous hydrogen chloride and a small amount of 4,4'-thiodiphenol crystals added, thus forming the requisite reaction system. A solution of 21.6 g (0.21 mole) of sulfur dichloride in 862 cc of cyclohexane was then added to the flask, with stirring, and the subject reaction begun. The temperature in the reaction vessel was maintained at about 25° C. The reaction was continued for about an hour. The entire reaction mixture was recovered and extracted with caustic, the caustic solution acidified, and the precipitated phenols extracted with ether. The material was then extracted with ether. The remaining 4,4'-thiodiphenol product had about a 90% selectivity, about an 87.3% yield, and contained about 0.1% polysulfides.

The above data clearly demonstrates that when a batch process is run according to the present invention, the subject reaction system again being employed, high yields, and selectivity, and a low polysulfide content will result.

EXAMPLE 3

This example illustrates the effect of employing sterically hindered and sterically nonhindered phenol to produce 4,4'-thiodiphenol materials.

In an attempt to prepare 4,4'-thiobis(2,6-di-tert-butyl phenol), 41.3 g (0.2 mole) of 2,6-di-tert-butylphenol was dissolved in 400 ml of heptane in a 1-liter round-bottom flask equipped with a stirrer, a condenser and drying tube. A sulfur dichloride solution was prepared by dissolving 6.4 cc (0.1 mole) of freshly distilled sulfur dichloride in 40 ml of heptane which was, in turn, added to the flask at room temperature with stirring. No reaction was noted after 1 hour at room temperature. The mixture was then heated to about 80°–90° C. for 1 hour. No reaction was observed.

Another run was made in an Erlenmyer flask, with the same amounts of the above phenolic compound and sulfur dichloride, but with only 80 ml of heptane. No reaction was apparent after the passage of about 1½ hours. Accordingly, the mixture was warmed to between about 50°–54° C. for half an hour. No hydrogen chloride gas was given off. A small amount of ferric chloride catalyst was added at room temperature. The temperature of the reaction was then again raised to about 53° C. for a period of about an hour and the mixture allowed to cool overnight. Some hydrogen chloride gas was evolved during heating and the color of the mixture turned much darker. After overnight cooling, the reaction was analyzed by gas chromatography. Analysis thereof indicated that most of the starting material had not been reacted. Another run was made using the same amounts of reactants while employing a total of 25 ml of petroleum ether as a solvent. One-half of the sulfur dichloride solution was added to the phenol solution at 16°–18° C. in about half an hour. This mixture was then refluxed at about 56° to 57° C. for half an hour, and then cooled to about 16° C. to 18° C. The remaining sulfur dichloride was added in about half an hour and the mixture again refluxed. Hydrogen chloride gas was driven off slowly during refluxing. The reaction mixture was further refluxed overnight and then analyzed by gas chromatograph. Analysis again showed that a considerable amount of starting material was still present in the reaction mixture.

The procedure employed in Example 2 was used, whereby 90.5 g (0.84 mole) of o-cresol in 783 cc of cyclohexane was combined with 21.6 g (0.21 mole) of sulfur dichloride in 861 cc of cyclohexane. 4,4'-thiobis-(o-cresol) crystals and a catalytic amount of hydrogen chloride were added as before. The 4,4'-monothiodiphenol-containing product formed, after extraction, was analyzed by gas chromatograph and found to have a selectivity of 93%, and a yield of 74.5%.

In a similar manner, 102 g (0.8 mole) of 2,6-xylenol in 778 cc of cyclohexane was combined with 21.6 g (0.21 mole) of sulfur dichloride in 862 cc of cyclohexane. Analysis of the resultant product shows a yield of about 95% and a selectivity of about 95% 4,4'-isomer.

The above results clearly demonstrate that sterically hindered phenols do not react with sulfur dichloride in a similar manner to sterically nonhindered phenols employed according to the process of the present invention, this being true even when a Lewis acid is employed along with the above sterically hindered phenols for purposes of initiating the reaction thereof.

EXAMPLE 4

This example illustrates the effect upon the formation of polysulfide by-products by varying the mole ratio of phenol to sulfur dichloride (stoichiometric ratio = 2:1).

A continuous reaction system, similar to that provided in Example 1, was employed varying the mole ratio of phenol with respect to sulfur dichloride, the results obtained being as follows:

| Phenol: Sulfur Dichloride (Mole Ratio) | Percent Polysulfide Formed |
| --- | --- |
| 2.7 | 2.4 |
| 3.0 | 0.8 |
| 3.3 | 0.3 to 0.6 |
| 4.0 | 0.2 to 0.4 |

By polarographic analysis, an average of 2.4% polysulfide by-products were found to be contained in the accrued TDP product prepared by employing a 2.7:1 mole ratio of phenol to sulfur dichloride. In contradistinction, when accrued products are prepared from 3.0:1, 3.3:1, or 4.0:1 ratios of phenol to sulfur dichloride, less than about 1% by weight polysulfide by-products were present in the recovered material.

EXAMPLE 5

The following table illustrates the effect on selectivity and yield of various saturated solvents employed within the scope of the present invention, each solvent having a different solubility parameter.

| Solvent | Solubility Parameter | Hydrogen Bonding Energy | Percent Selectivity | Percent Yield |
|---|---|---|---|---|
| n-Pentane | 7.0 | Low | 94 | 71.5 |
| n-Heptane | 7.4 | Low | 92 | 79.1 |
| Methylcyclohexane | 7.8 | Low | 90 | 81.9 |
| Methylcyclopentane | 7.9 | Low | 90 | 81.9 |
| Cyclohexane | 8.2 | Low | 90 | 87.2 |
| Butyl Chloride | 8.3 | Low | 84 | 82.5 |
| Carbon Tetrachloride | 8.6 | Low | 85 | 76.0 |

The above results clearly indicate that high yields and selectivity will result when the requisite solvent is employed within the scope of the subject invention.

EXAMPLE 6

The optimum temperature range for a given reaction within the scope of the present invention was analyzed by monitoring the reaction of phenol and sulfur dichloride. Reaction was continuously run in a similar manner to the reaction outlined in Example 1, varying only the reaction temperature over a period of time. The results based on the percent polysulfide generated at a given temperature are as follows:

| Temperature in Degree Centigrade | Percent Polysulfide |
|---|---|
| 10 | 2.4 |
| 26 | 0.2 to 0.5 |
| 38 | 2.3 |
| 44 | 4.3 |

When the temperature is maintained at about 26°C., the product exhibited a polysulfide content, determined by polarographic analysis, of about 0.2% to 0.5% by weight based on the total yield of material produced. However, when the temperature was dropped to 10° C., a 2.4% yield of polysulfides was produced due to the separation of phenols at that temperature, which resulted in a lower molar ratio of phenol to sulfur dichloride actually present in the subject reaction system. Moreover, when the temperature was raised to 38° C. and 44° C., respectively, polysulfide yields of 2.3%, respectively, were observed.

The above results indicate that the amount of polysulfide by-products will be significantly reduced in the above described reaction of phenol and sulfur dichloride under the above reaction conditions.

The terms and expressions which have been employed in the foregoing abstract and specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A process for selectively producing 4,4'-monothiodiphenol compounds in high yields, which comprises:
   a. forming a reaction system having a reactant portion including either one of an unsubstituted and sterically nonhindered ortho-substituted phenolic compound and sulfur dichloride, an initiation promoter portion including a crystalline additive of said 4,4'-monothiodiphenolic product compound, and a catalytic amount of anhydrous hydrogen chloride, and a solvent portion including a substantially saturated compound having a solubility parameter of at least about 7.0 $(Cal/cc)^{1/2}$ up to 9.0 $(Cal/cc)^{1/2}$ and a low degree of hydrogen bonding;
   b. reacting said phenolic compound and sulfur dichloride, in the presence of said initiation promoter and solvent portions, respectively at a temperature greater than the freezing point of the phenolic compound and solvent portion, and less than the temperature at which a substantial amount of undesirable, noncrystalline by-product will be produced, to produce said 4,4'-monothiodiphenolic, selective, high yield product; and
   c. recovering said 4,4'-monothiodiphenolic product from said reaction system.

2. The selective 4,4'-monothiodiphenol formation process of claim 1 further characterized in that said product is recovered in high yields, on substantial completion of said phenolic compound-sulfur dichloride reaction step, without requiring any additional reaction steps.

3. The selective 4,4'-monothiodiphenol formation process of claim 1, wherein the reaction system contains a minimum amount of undesirable by-products, including polysulfides, non-para- substituted thiodiphenolic compounds, chlorinated phenolic products, sulfonium compounds and polymeric materials.

4. The selective 4,4'-monothiodiphenol formation process of claim 1, wherein the selectivity of said product formed is at least about 80% by weight, based on the total weight of recovered material.

5. The selective 4,4'-monothiodiphenol formation process of claim 1, wherein the yield of said product formed is at least about 70% by weight.

6. The selective 4,4'-monothiodiphenol formation process of claim 1, wherein the selectivity of said product formed is at least about 90% by weight, based on the total weight of recovered material.

7. The selective 4,4'-monothiodiphenol formation process of claim 1, wherein the yield of said product formed is at least about 80% by weight.

8. The selective 4,4'-monothiodiphenol formation process of claim 1, wherein the amount of polysulfides present in the product recovered is less than about 1.0% by weight, based on the total weight of recovered material.

9. The selective 4,4'-monothiodiphenol formation process of claim 1, wherein the amount of polysulfides present in the product recovered is less than about 0.5% by weight, based on the total weight of recovered material.

10. The selective 4,4'-monothiodiphenol formation process of claim 1, wherein said substituted phenolic compound is further characterized in that the pendant groups substituted in the ortho- position on said phenolic ring include lower alkyl groups having from 1 to 3 carbon atoms, the total number of said carbon atoms present in said alkyl groups of the substituted phenolic compound being from 1 to 5.

11. The selective 4,4'-monothiodiphenol formation process of claim 1, wherein the phenolic compound is selected from the group consisting of phenol, o-cresol, and 2,6-xylenol.

12. The selective 4,4'-monothiodiphenol formation process of claim 1, wherein the phenolic compound is phenol, and the high yield 4,4'-monothiodiphenolic product selectively formed is 4,4'-thiodiphenol.

13. The selective 4,4'-monothiodiphenol formation process of claim 1, wherein the solvent portion of said reaction system has a solubility parameter of at least about 7.5 and up to about 8.5 $(Cal/cc)^{1/2}$.

14. The selective 4,4'-monothiodiphenol formation process of claim 1, wherein the solvent portion employed is a compound selected from the group consisting of substituted or unsubstituted cycloaliphatics, aliphatics, halogenated aliphatics, and mixtures thereof.

15. The selective 4,4'-monothiodiphenol formation process of claim 1, wherein the solvent portion employed is a compound selected from the group consisting of hexane, heptane, cyclohexane, methylcyclopentane, methylcyclohexane, and mixtures thereof.

16. The process of claim 1, wherein the selective thiodiphenol formation process is carried out in a continuous manner.

17. The continuous selective 4,4'-monothiodiphenol formation process of claim 16 further characterized in that the contact time for completion of the above formation process is not more than about 0.5 hour.

18. The continuous process of claim 17, wherein said contact time is not more than about 0.25 hour.

19. The selective 4,4'-monothiodiphenol formation process of claim 1, wherein said reaction system is formed by admixing the respective reactant, initiation promoter, and solvent portions together, one with the other.

20. The selective 4,4'-monothiodiphenol formation process of claim 1, wherein the 4,4'-monothiodiphenol crystals are present in the initiation promoter portion in an amount sufficient for saturation of said reaction system.

21. The selective formation process of claim 20, wherein an excess amount of said crystals are present in said reaction system.

22. The selective 4,4'-monothiodiphenol formation process of claim 1, wherein hydrogen chloride is present in the initiation promoter portion in an amount sufficient to saturate the reaction system.

23. The selective 4,4'-monothiodiphenol formation process of claim 1, wherein the molar ratio of phenolic compound to sulfur dichloride in the reactant portion of the reaction system is at least a minimum of about 3:1, up to a ratio of about 10:1.

24. The selective formation process of claim 23, wherein the minimum ratio is at least about 4:1.

25. The selective 4,4'-monothiodiphenol formation process of claim 1, wherein the concentration of said phenolic compound in said reaction system is greater than about 0.5% by weight, based on the weight of solvent, and less than an amount which would cause the formation of undesirable, noncrystalline by-products.

26. The selective thiodiphenolic formation process of claim 1, wherein the concentration of the phenolic compound in the reactant system is at least about 1% and up to about 20% by weight, based on the total weight of the reaction system.

27. The selective thiodiphenolic formation process of claim 1, wherein the reaction temperature is greater than the freezing point of the reaction solvent and less than a temperature at which a substantial amount of undesirable noncrystalline by-product will be produced.

\* \* \* \* \*